United States Patent [19]
Lord et al.

[11] Patent Number: 5,482,473
[45] Date of Patent: Jan. 9, 1996

[54] FLEX CIRCUIT CONNECTOR

[75] Inventors: Peter C. Lord, Santa Clarita; William P. Van Antwerp, Brentwood; John J. Mastrototaro, Los Angeles; Paul S. Cheney, II, Beverly Hills; Nannette M. Schnabel, Valencia, all of Calif.

[73] Assignee: Minimed Inc., Sylmar, Calif.

[21] Appl. No.: 239,960

[22] Filed: May 9, 1994

[51] Int. Cl.⁶ ....................................... H01R 9/09
[52] U.S. Cl. ................................. 439/67; 439/91
[58] Field of Search ................... 439/67, 66, 77, 439/91, 591

[56] References Cited

U.S. PATENT DOCUMENTS

| | | | |
|---|---|---|---|
| 4,495,917 | 1/1985 | Byers | 439/289 |
| 4,975,068 | 12/1990 | Squires | 439/67 |

*Primary Examiner*—Neil Abrams
*Attorney, Agent, or Firm*—Kelly Bauersfeld & Lowry

[57] ABSTRACT

A connector is provided for electrical connection to a flex circuit in a hermetically sealed manner. The flex circuit comprises thin film conductors encased between layers of insulative material, and including a proximal end with conductive contact pads exposed through one of the insulative layers. In a preferred form, the proximal ends of the two flex circuits are assembled in face-to-face relation and compressed by a clamp fixture against opposite side faces of a compressible terminal block. The terminal block is formed from a resilient insulative elastomer such as silicone rubber with embedded conductive strips having opposite edges exposed at the opposite side faces of the terminal block for electrically connecting aligned pairs of the contact pads on the two flex circuits. The exposed edges of the conductive strips are circumscribed by the insulative elastomer which engages the flex circuits with a footprint circumscribing the exposed contact pads, whereby the terminal block hermetically seals the interface between the conductive strips and the contact pads.

9 Claims, 2 Drawing Sheets

FLEX CIRCUIT CONNECTOR

BACKGROUND OF THE INVENTION

This invention relates generally to connector devices for electrically connecting flexible circuit structures of the type having thin film conductors encased between relatively thin film layers of insulative material. More specifically, this invention relates to an improved connector for quick and easy coupling with a flex circuit in conductive and hermetically sealed relation.

Thin film flex circuits are generally known in the art for carrying electrical signals in a variety of compact electronics applications. Such devices may comprise a plurality of thin conductors formed on a relatively thin base layer of insulative material, such as polyimide sheet or the like. The conductors are then covered in turn by an upper or overlying layer of the insulative material, to form an elongated and relatively flexible circuit structure. At appropriate points along the length of the structure, apertures are formed in one of the insulation layers to expose portions of the conductors in order to permit electrical connection of the conductors to other electronic components. The exposed conductors are often referred to as contact pads and, in most cases, are located near the proximal and distal ends of the flex structure.

In some operating environments, flex circuits are used to carry electrical signals of extremely low power. For example, flex circuit technology has been adapted to fabricate relatively small and flexible electrochemical thin film sensors for use in a variety of applications, such as transcutaneous placement of sensor electrodes in direct contact with patient blood so that periodic blood chemistry readings can be obtained over an extended period of time. See, for example, U.S. Pat. No. 5,391,250 entitled METHOD OF FABRICATING THIN FILM SENSORS. In electrochemical sensors of this type, electrode chemistries are applied to exposed contact pads at a distal end of a flex circuit, to provide sensor electrodes adapted for transcutaneous placement. Additional exposed contact pads at a proximal end of the flex circuit are provided for electrical connection to appropriate monitoring equipment. The low current signals inherent in such sensors mandate a high quality electrical connection between the sensor electrodes and the monitoring equipment, with minimum electrical leakage. In addition, it is important for this electrical connection to be hermetically sealed, in order to safeguard the electrical connection against moisture contamination while permitting substantially normal daily patient activities such as bathing and showering, etc.

The present invention relates specifically to an improved flex circuit connector adapted for quick and easy connection to one or more flex circuits to provide a high quality electrical connection which is hermetically sealed.

SUMMARY OF THE INVENTION

In accordance with the invention, a flex circuit connector is provided for electrical connection to one or more flex circuits in hermetically sealed relation. The connector comprises a terminal block formed from an insulative elastomer such as silicone rubber, with conductive strips embedded therein and having exposed edges at opposite side faces of the terminal block. The terminal block is adapted in one preferred form to fit between the proximal ends of a pair of flex circuits having exposed conductive contact pads presented in face-to-face relation for engaging the opposite side faces of the terminal block. Clamp means in the form of a clamp fixture compressively retains the proximal ends of the flex circuits against the terminal block, with aligned pairs of contact pads on the two flex circuits being electrically interconnected by the conductive strips. Importantly, the conductive strips of the terminal block are circumscribed by the insulative elastomer which engages the terminal blocks along a footprint circumscribing the exposed contact pads, such that the terminal block also hermetically seals the interface between the conductive strips and the contact pads.

The two flex circuits, in a preferred form, each include a plurality of thin film conductors embedded or encased between thin film layers of insulative material, such as polyimide film. One of the insulative layers of each flex circuit has a plurality of apertures formed therein at the proximal end thereof to expose the conductive contact pads. These conductive contact pads are physically spaced from one another with a pitch spacing for contacting the conductive strips within the terminal block, whereby the conductive strips electrically interconnect aligned pairs of the contact pads on the two flex circuits. Alternately, the connector may be used for electrical and hermetically sealed coupling with a single flex circuit.

The clamp fixture comprises a lower base plate and an upper clamp plate in combination with lever means for pressing the clamp plate toward the base plate. The proximal end of the two flex circuits are assembled with their exposed contact pads in face-to-face relation seated against the opposite side faces of the terminal block, and the lever means is operated to compressively retain the flex circuits against the terminal block. The magnitude of terminal block compression is chosen to provide high quality electrical interconnection in combination with a hermetic seal circumscribing the contact pads on each flex circuit. In one preferred form, the clamp means is designed to compress the terminal block in excess of fifteen percent compression.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
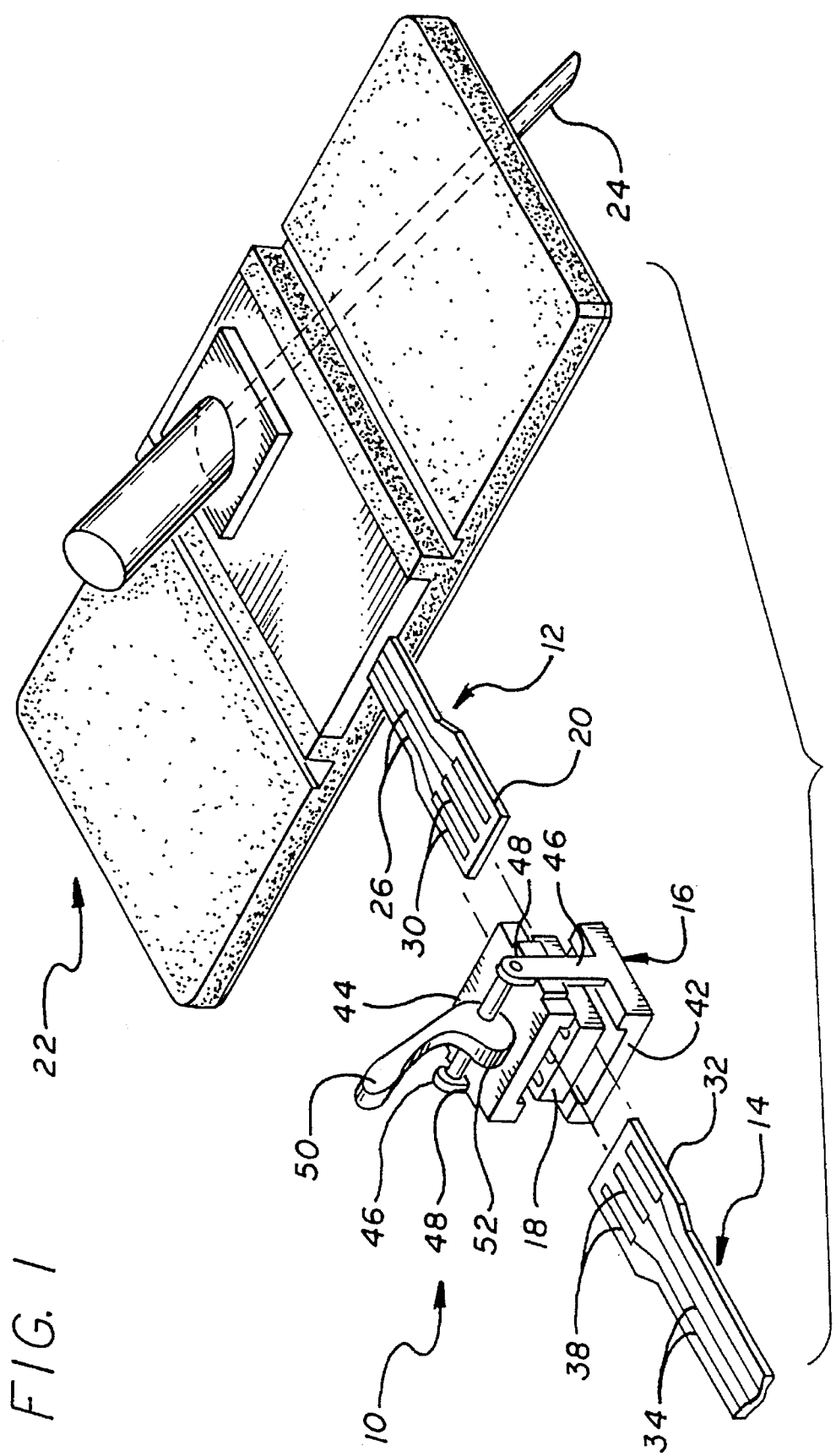
FIG. 1 is an exploded perspective view illustrating a flex circuit connector embodying the novel features of the invention.

As shown in the exemplary drawings, a flex cirucit connector referred to generally by the reference numeral 10 is provided for interconnecting a pair of flex circuits 12 and 14. The connector 10 includes a clamp fixture 16 for compressedly retaining adjacent proximal ends of the flex circuits 12 and 14 against opposite side faces of a terminal block 18.

Although the flex circuit connector 10 of the present invention has utility in a variety of electronic devices and systems, the illustrative drawings show the invention for electrically connecting an electrochemical sensor with a flex circuit used to convey electrical signals to an appropriate monitor device (not shown). FIG. 1 shows the electrochemical sensor in the form of the flex circuit 12 provided in a transcutaneous insertion set 22 of the type described in copending U.S. Pat. No. 5,390,671, entitled TRANS CUTANEOUS SENSOR INSERTION SET, which is incorporated by reference herein. In general terms, for purposes of clarity and completeness of description, the insertion set 22 includes an insertion needle 24 for transcutaneous placement of a distal end of the flex circuit 12 having sensor electrodes exposed for directly contacting patient blood. A plurality of thin film conductors 26 are encased between relatively thin layers of insulative material, such as polyimide sheet, for conveying electrical signals along the length of the flex circuit 12 from the distal end electrodes to the proximal end 20 thereof. The upper layer of insulative film material has a plurality of small openings 28 formed therein (FIG. 3) to expose conductive contact pads 30 at the proximal ends of the conductors 26.

Figure 3:
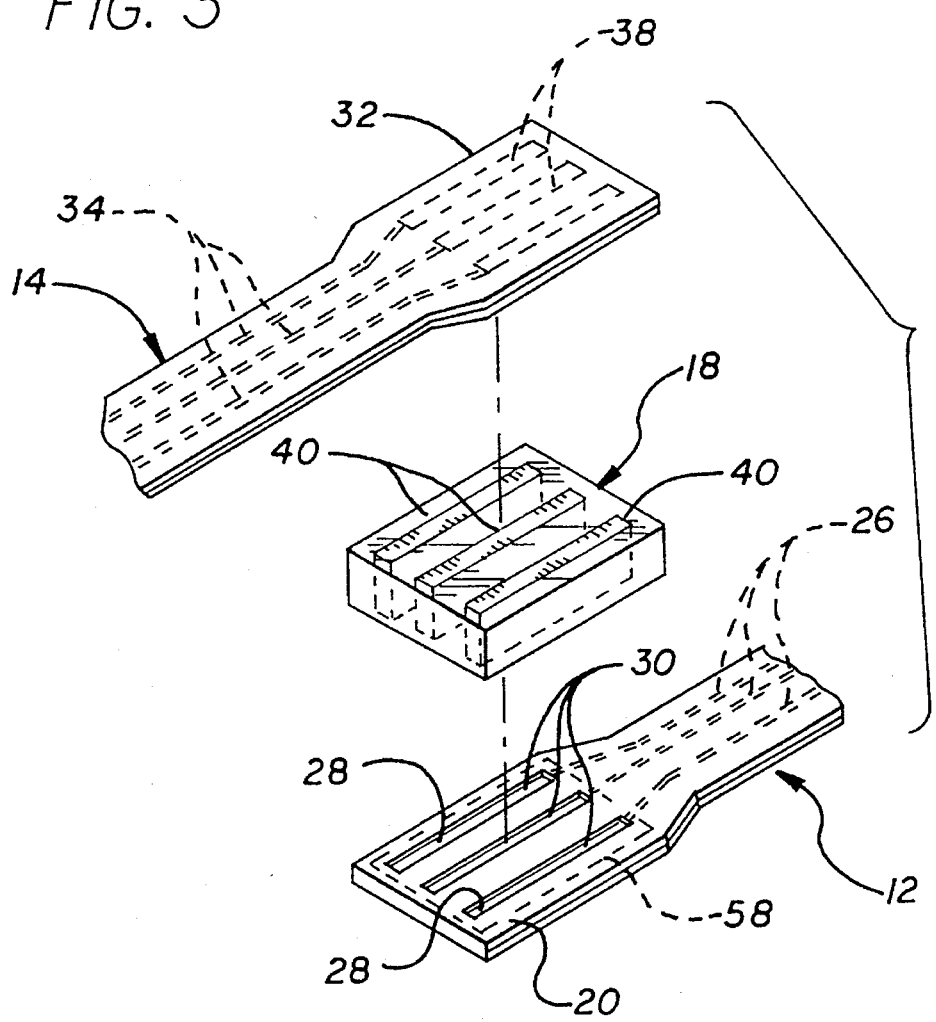
FIG. 3 is an exploded perspective view illustrating the proximal ends of a pair of flex circuits assembled in face-to-face relation with a terminal block interposed therebetween.

As shown in FIG. 3, the proximal end 32 of the second flex circuit 14 has a similar construction, to include a plurality of thin film conductors 34 encased between upper and lower insulative layers of polyimide film sheet or the like. At the proximal end 32, the lower insulative layer has openings formed therein to expose contact pads 38. The flex circuit 14 has a distal end (not shown) adapted for connection to the monitor device, so that patient blood chemistry can be monitored.

In general terms, the connector 10 of the present invention is provided for quickly and easily establishing a high quality electrical connection between the contact pads 30 and 38 at the proximal ends 20, 32 of the two flex circuits. In addition, the connector 10 provides a hermetic seal which circumscribes the conductive interface between the exposed contact pads 30 and 38 on the flex circuits. Alternately, it will be understood that the connector 10 may be used for electrical and hermetically sealed coupling with a single flex circuit. In either case, electrical leakage at the connection is substantially minimized or eliminated to prevent erroneous readings as a result of noise and other interference. Moreover, in the illustrative application, the patient (not shown) may engage in substantially normal daily activities, including bathing and showering, exercising, etc., since the connector 10 prevents moisture ingress to the electrical interface.

Figure 2:
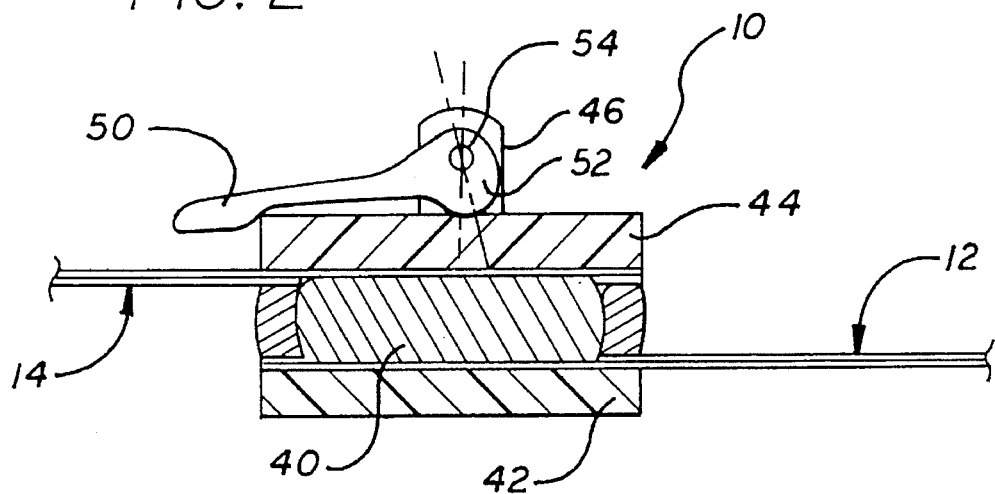
FIG. 2 is an enlarged fragmented vertical sectional view, illustrating the flex circuit connector in a closed position electrically interconnecting two flex circuits in hermetically sealed relation.

As shown best in FIGS. 2 and 3, the terminal block 18 comprises a generally rectangular plate-shaped body formed from a resilient elastomer such as cured silicone rubber or the like. The block 18 encases a plurality of elongated strips 40 of conductive material such as a carbon-based or other selected conductor material. These conductive strips 40 extend through the block 18 to define exposed edges at the upper and lower faces of the terminal block. Moreover, the number of conductive strips 40 and the pitch spacing therebetween are designed for one-to-one contact between each conductive strip and a respective aligned pair of the contact pads 30 and 38 on the two flex cables. Importantly, the silicone elastomer material of the block 18 perimetrically circumscribes the conductive strips 40 along an uninterrupted line adapted to sealingly engage the flex circuits 12 and 14 along a line or footprint which circumscribes the contact pads. Thus, when the terminal block 18 is compressedly retained between the proximal ends of the flex circuits, the terminal block 18 hermetically seals the contact pads against moisture ingress.

The clamp fixture 16 comprises one exemplary structure for providing a mechanical advantage to compressedly retain the proximal ends 20, 32 of the flex circuits 12, 14 against the opposite side faces of the terminal block 18. As shown, the fixture 16 includes a rigid base plate 42 in combination with an overlying rigid clamp plate 44. A pair of support arms 46 project upwardly from opposite sides of the base plate 42 for slide-fit reception through track slots 48 at opposite sides of the clamp plate 44. A cam lever 50 has a cam lobe 52 carried on a pivot pin 54 which extends between the upper ends of the support arms 46. The cam lever 50 is movable to rotate the cam lobe 52 in a manner pressing downwardly on the clamp plate 44.

In use of the illustrative embodiment, the proximal end 20 of the flex circuit 12 is fitted into the clamp fixture 16, in a position between the support arms 46 with the contact pads 20 exposed upwardly. The proximal end 32 of the second flex circuit 14 is fitted into the fixture, in face-to-face relation with the underlying flex circuit 12, so that the exposed contact pads 38 are presented downwardly. The terminal block 18 is interposed between the proximal ends of the fles circuits, oriented so that the conductive strips 40 are in parallel with the contact pads on the flex circuits. The cam lever 50 is rotated to urge the cam lobe 52 against the clamp plate 44, thereby pressing the clamp plate downwardly to compress the terminal block 18 between the flex circuits.

With appropriate compression of the terminal block, preferably in excess of fifteen percent compression, the conductive strips 40 are electrically interconnected between aligned pairs of the contact pads on the two flex circuits, to provide a high quality electrical connection with little or no current leakage. Moreover, the size and shape of the terminal block is sufficient to engage the flex circuits along a footprint 58 (FIG. 3) which circumscribes the contact pads so that the electrical connection is hermetically sealed. Conveniently, the cam lever 50 moves the lobe 52 over-center, as viewed in FIG. 2, so that the clamp fixture 16 is effectively locked in the closed position.

A variety of further modifications and improvements to the flex circuit connector of the present invention will be apparent to those skilled in the art. Accordingly, no limitation on the invention is intended by way of the foregoing description and accompanying drawings, except as set forth in the appended claims.

What is claimed is:

1. A flex circuit connector for interconnecting a pair of flex circuits each having a proximal end with exposed conductive contact pads thereon, the contact pads of each flex circuit exposed through openings in a layer of the flex circuit, said flex circuit connector comprising:

a zebra terminal block having a body formed from a resilient insulative elastomer to define opposite side faces, and a plurality of conductive strips embedded within said body and having opposite edges exposed at said opposite side faces, said body defining insulative material circumscribing said conductive strips along an uninterrupted line at both of said opposite side faces; and clamp means for clamping the proximal ends of the flex circuits in face-to-face relation in engagement with said opposite side faces of said body and with said contact pads in conductive engagement with said conductive strips, said body engaging each of said flex circuits in hermetically sealed relation along a line of contact circumscribing the contact pads.

2. The ribbon cable connection of claim 1 wherein said clamp means is releasable.

3. The ribbon cable connector of claim 1 wherein said body of said terminal block is formed from silicone rubber.

4. The ribbon cable connector of claim 1 wherein said clamp means is adapted to compress said terminal block by a factor of at least fifteen percent compression.

5. A flex circuit connector for electrical and hermetically sealed connection to a flex circuit having a proximal end with a plurality of exposed contact pads thereon, the contact pads of each exposed through openings in a layer of the flex circuit, said flex circuit connector comprising:

a terminal block having a body formed from a resilient insulative elastomer and a plurality of conductive strips embedded within said body, said conductive strips having edges exposed at one side face of said body, and said body defining insulative material circumscribing the exposed edges of said conductive strips at said one side face; and clamp means for clamping the proximal end of the flex circuit against said one side face of said body, with said contact pads respectively and conductively engaging said conductive strips, and with said body engaging the flex circuit in hermetically sealed relation along a line of contact circumscribing the contact pads.

6. The ribbon cable connector of claim 5 wherein said clamp means is releasable.

7. The ribbon cable connector of claim 5 wherein said body of said terminal block is formed from silicone rubber.

8. The ribbon cable connector of claim 5 wherein said clamp means is adapted to compress said terminal block by a factor of at least fifteen percent compression.

9. A flex circuit connector for interconnecting a pair of flex circuits each having a proximal end with at least one exposed conductive contact pad thereon, the contact pads of each flex circuit exposed through openings in a layer of the flex circuit, said flex circuit connector comprising:

a terminal block having a body formed from a resilient insulative elastomer to define opposite side faces, and at least one conductive strip embedded within said body and having opposite edges exposed at said opposite side faces, said body defining insulative material circumscribing said conductive strip along an uninterrupted line at both of said opposite side faces; and clamp means for clamping the proximal ends of the flex circuits in face-to-face relation in engagement with said opposite side faces of said body and with said contact pads in conductive engagement with said at least one conductive strip, said body engaging each of said flex circuits in hermetically sealed relation along a line of contact circumscribing the contact pads.

* * * * *